United States Patent
Horne et al.

(10) Patent No.: US 9,700,647 B2
(45) Date of Patent: *Jul. 11, 2017

(54) ULTRAVIOLET GERMICIDAL IRRADIATION SYSTEM

(71) Applicant: PURGENIX, INC., Atlanta, GA (US)

(72) Inventors: Joel E. Horne, Lawrenceville, GA (US); Richard P. Sutton, Murray, KY (US)

(73) Assignee: Purgenix, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/538,471

(22) Filed: Nov. 11, 2014

(65) Prior Publication Data

US 2015/0129782 A1    May 14, 2015

Related U.S. Application Data

(63) Continuation of application No. 13/742,035, filed on Jan. 15, 2013, now Pat. No. 8,883,081, which is a
(Continued)

(51) Int. Cl.
*A61L 9/20* (2006.01)

(52) U.S. Cl.
CPC ...................... *A61L 9/20* (2013.01)

(58) Field of Classification Search
CPC ..... A61L 2/08; A61L 2/10; A61L 9/18; A61L 9/20
See application file for complete search history.

(56) References Cited

U.S. PATENT DOCUMENTS 4,751,627 A * 6/1988 Usher ........................ 362/421
4,979,081 A   12/1990 Leach et al.
(Continued)

FOREIGN PATENT DOCUMENTS

JP       07174401       7/1995
WO       03095030       11/2003

OTHER PUBLICATIONS

"Defining The Effectiveness of UV Lamps Installed in Circulating Air Ductwork," by Douglas Van Osdell and Karin Foarde, Prepared for the Air-Conditioning and Refrigeration Institute Under ART 21-CR Program Contract No. 610-40030, Nov. 2002.
(Continued)

*Primary Examiner* — Regina M Yoo
(74) *Attorney, Agent, or Firm* — Taylor English Duma LLP

(57) ABSTRACT

A modular germicidal light grid system for use inside an air treatment apparatus that has a plenum in which a stream of air is enclosed. The system comprises at least one elongate member and at least one lamp assembly. Each lamp assembly comprises a housing defining at least one socket and is mounted to one elongate member at a predetermined position. The system further comprises at least one linear germicidal light source. Each light source has a longitudinal axis and a distal end constructed and arranged to mount within one socket of the housing. The elongate member is mounted within the plenum and the lamp assembly is mounted to the elongate member such that the longitudinal axis of the light source extends therein the stream of air and is positioned at an acute light angle relative to the direction of flow of the stream of air.

20 Claims, 11 Drawing Sheets

Related U.S. Application Data continuation of application No. 13/229,293, filed on Sep. 9, 2011, now Pat. No. 8,354,060, which is a continuation of application No. 10/932,997, filed on Sep. 2, 2004, now Pat. No. 8,038,949.

(56) References Cited

U.S. PATENT DOCUMENTS

| | | | |
|---|---|---|---|
| 5,208,461 A * | 5/1993 | Tipton | 250/436 |
| 5,334,347 A | 8/1994 | Hollander | |
| 5,418,370 A * | 5/1995 | Maarschalkerweerd | 250/431 |
| 5,780,860 A | 7/1998 | Gadgil et al. | |
| 5,817,276 A | 10/1998 | Fencl et al. | |
| 5,866,076 A | 2/1999 | Fencl et al. | |
| 5,997,619 A * | 12/1999 | Knuth et al. | 96/224 |
| 6,245,293 B1 | 6/2001 | Fencl et al. | |
| 6,264,888 B1 | 7/2001 | Palestro et al. | |
| 6,267,924 B1 | 7/2001 | Fencl et al. | |
| 6,280,686 B1 | 8/2001 | Scheir et al. | |
| 6,313,470 B1 | 11/2001 | Fencl et al. | |
| 6,342,188 B1 * | 1/2002 | Pearcey et al. | 422/186.3 |
| 6,372,186 B1 | 4/2002 | Fencl et al. | |
| 6,423,882 B1 | 7/2002 | Fencl | |
| 6,500,267 B1 | 12/2002 | Fencl | |
| 6,589,476 B1 * | 7/2003 | Fencl | 422/4 |
| 6,627,000 B2 | 9/2003 | Fencl et al. | |
| 6,630,678 B2 * | 10/2003 | Guzorek | 250/432 R |
| 6,932,494 B1 | 8/2005 | Burnett et al. | |
| 8,038,949 B2 * | 10/2011 | Horne et al. | 422/121 |
| 8,354,060 B2 * | 1/2013 | Horne et al. | 422/121 |
| 8,883,081 B2 * | 11/2014 | Home et al. | 422/121 |
| 2002/0070177 A1 * | 6/2002 | Kozlowski | 210/748 |
| 2002/0104972 A1 | 8/2002 | Guzorek | |
| 2003/0019505 A1 | 1/2003 | Scheir et al. | |
| 2005/0069463 A1 * | 3/2005 | Kurtz et al. | 422/121 |
| 2005/0263716 A1 | 12/2005 | From et al. | |

OTHER PUBLICATIONS

Horne, Joel E.; Advisory Action for U.S. Appl. No. 10/932,997, filed Sep. 2, 2004, mailed Oct. 8, 2009, 3 pgs.
Horne, Joel E.; Final Office Action for U.S. Appl. No. 10/932,997, filed Sep. 2, 2004, mailed Jul. 21, 2010, 30 pgs.
Horne, Joel E.; Final Office Action for U.S. Appl. No. 10/932,997, filed Sep. 2, 2004, mailed Jul. 30, 2009, 27 pgs.
Horne, Joel E.; Issue Notification for U.S. Appl. No. 10/932,997, filed Sep. 2, 2004, mailed Sep. 28, 2011, 1 pg.
Horne, Joel E.; Non-Final Office Action for U.S. Appl. No. 10/932,997, filed Sep. 2, 2004, mailed Jan. 5, 2009, 28 pgs.
Horne, Joel E.; Non-Final Office Action for U.S. Appl. No. 10/932,997, filed Sep. 2, 2004, mailed Nov. 13, 2009, 23 pgs.
Horne, Joel E.; Non-Final Office Action for U.S. Appl. No. 10/932,997, filed Sep. 2, 2004, mailed Feb. 15, 2011, 25 pgs.
Horne, Joel E.; Notice of Allowability for U.S. Appl. No. 10/932,997, filed Sep. 2, 2004, mailed Jul. 28, 2011, 4 pgs.
Horne, Joel E.; Notice of Allowance for U.S. Appl. No. 10/932,997, filed Sep. 2, 2004, mailed Jun. 10, 2011, 9 pgs.
Horne, Joel E.; Restriction Requirement for U.S. Appl. No. 10/932,997, filed Sep. 2, 2004, mailed Mar. 11, 2008, 7 pgs.
Horne, Joel E.; Restriction Requirement for U.S. Appl. No. 10/932,997, filed Sep. 2, 2004, mailed Jul. 25, 2008, 8 pgs.
Horne, Joel E.; U.S. Patent Application entitled: Ultraviolet Germicidal Irradiation System having U.S. Appl. No. 10/932,997, filed Sep. 2, 2004, 42 pgs.
Horne, Joel E.; Issue Notification for U.S. Appl. No. 13/229,293, filed Sep. 9, 2011, mailed Dec. 22, 2012, 1 pg.
Horne, Joel E.; Non-Final Office Action for U.S. Appl. No. 13/229,293, filed Sep. 9, 2011, mailed Dec. 30, 2011, 27 pgs.
Horne, Joel E.; Notice of Allowance for U.S. Appl. No. 13/229,293, filed Sep. 9, 2011, mailed Sep. 14, 2012, 8 pgs.
Horne, Joel E.; U.S. Continuation Application entitled: Ultraviolet Germicidal Irradiation System having U.S. Appl. No. 13/229,293, filed Sep. 9, 2011, 33 pgs.
Horne, Joel E.; Final Office Action for U.S. Appl. No. 13/742,035, filed Jan. 15, 2013, mailed Mar. 21, 2014, 6 pgs.
Horne, Joel E.; Issue Notification for U.S. Appl. No. 13/742,035, filed Jan. 15, 2013, mailed Oct. 22, 2014, 1 pg.
Horne, Joel E.; Non-Final Office Action for U.S. Appl. No. 13/742,035, filed Jan. 15, 2013, mailed Oct. 7, 2013, 7 pgs.
Horne, Joel E.; Notice of Allowance for U.S. Appl. No. 13/742,035, filed Jan. 15, 2013, mailed Jul. 8, 2014, 9 pgs.
Horne, Joel E.; U.S. Continuation Application entitled: Ultraviolet Germicidal Irradiation System having U.S. Appl. No. 13/742,035, filed Jan. 15, 2013, 28 pgs.

* cited by examiner

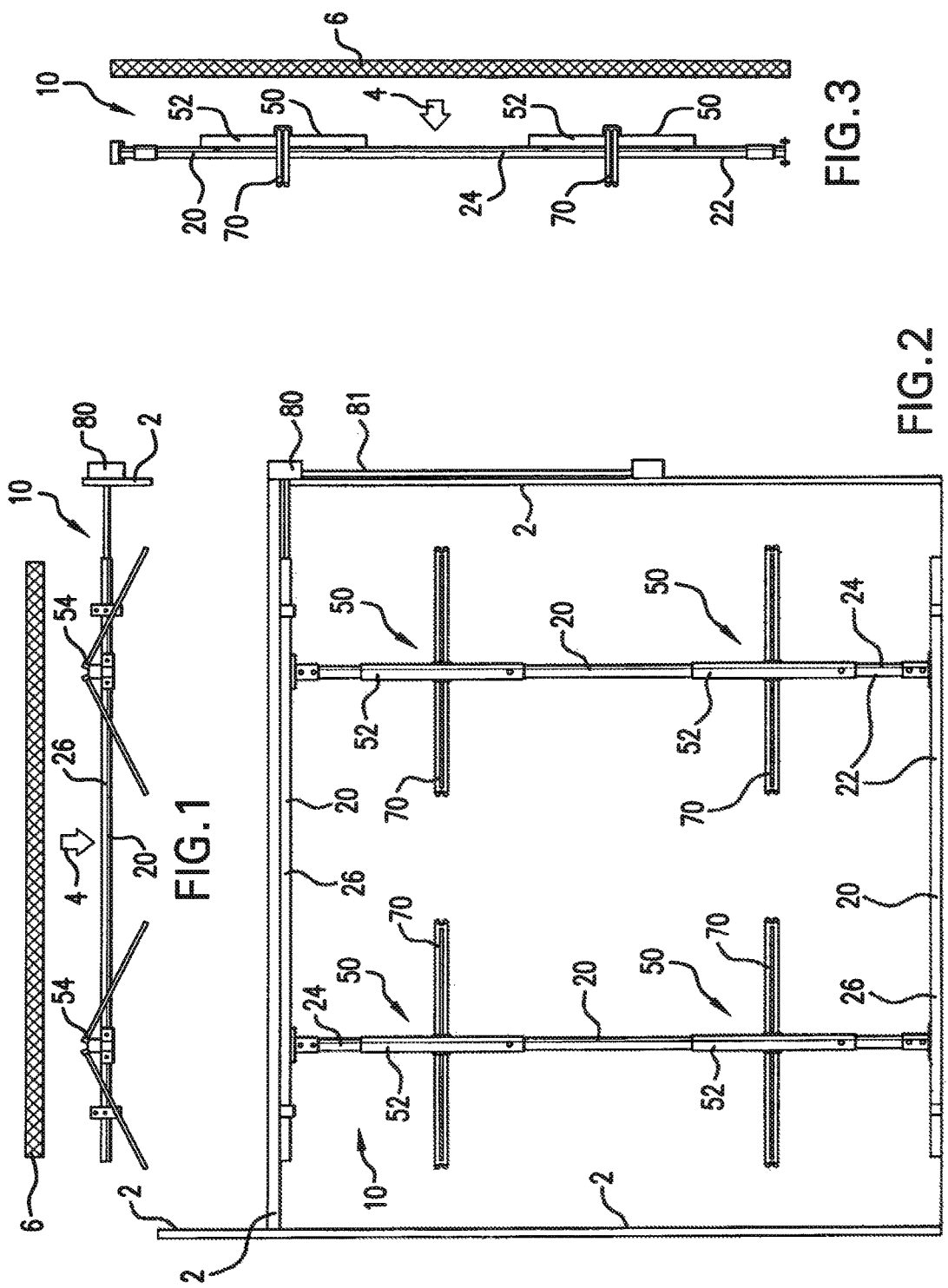

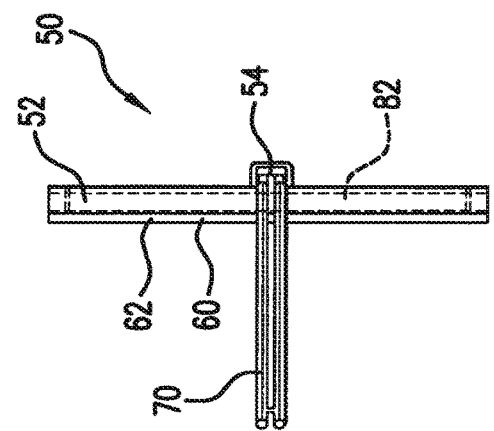
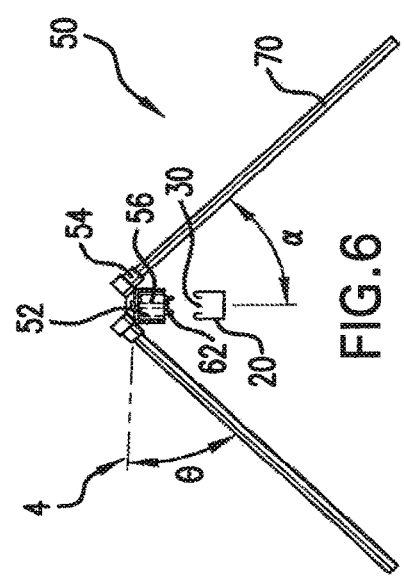
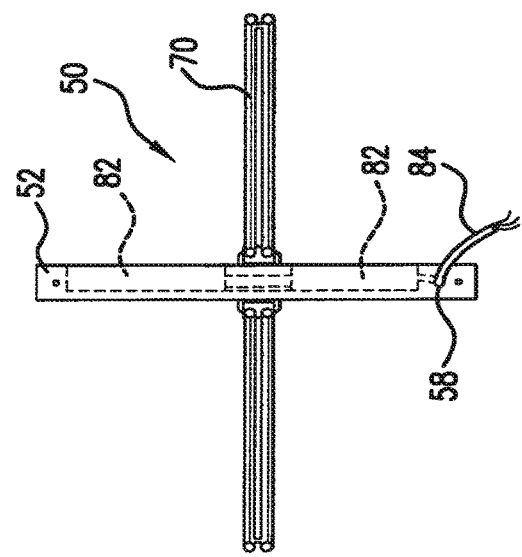

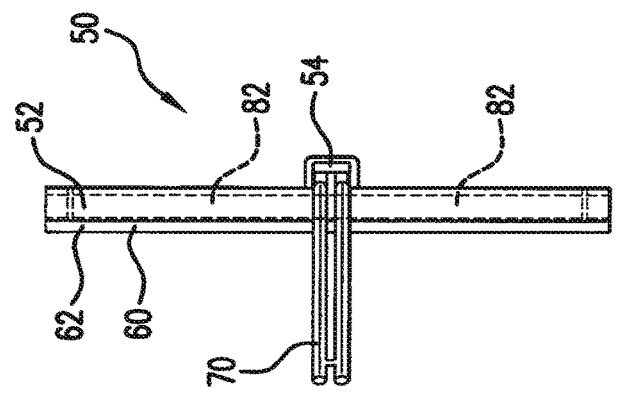
FIG. 9
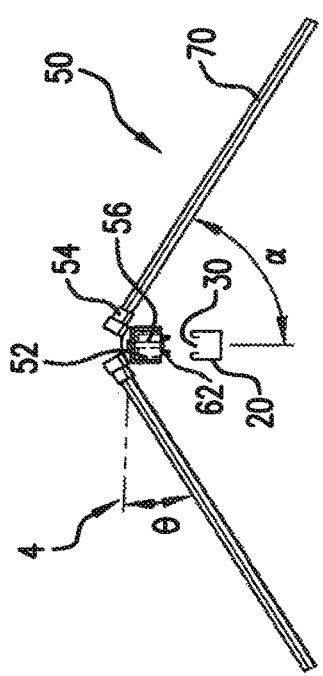
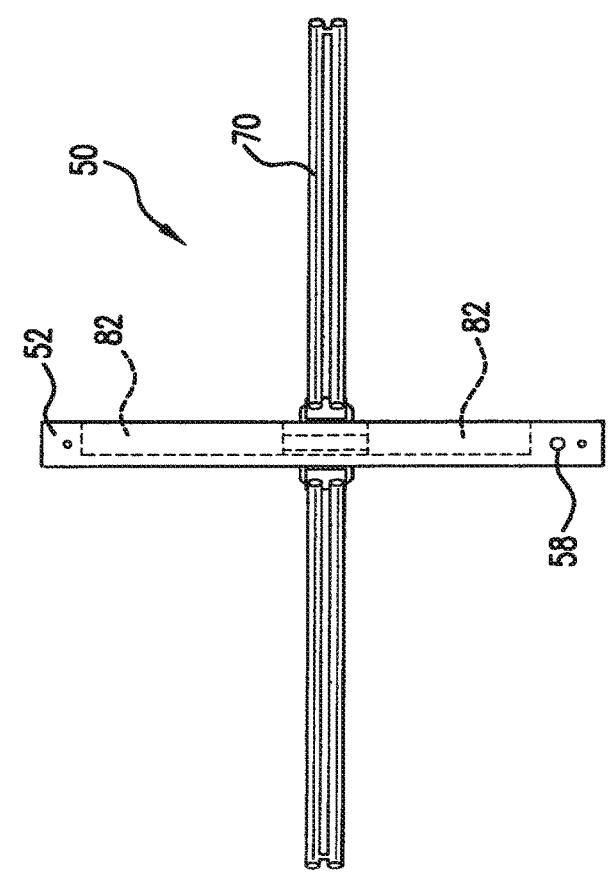
FIG. 10
FIG. 11

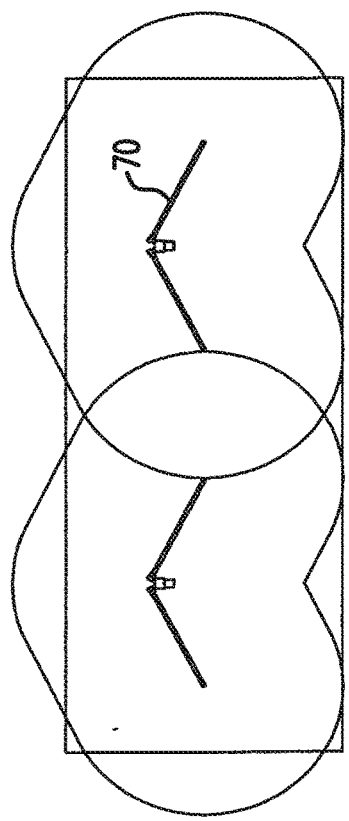
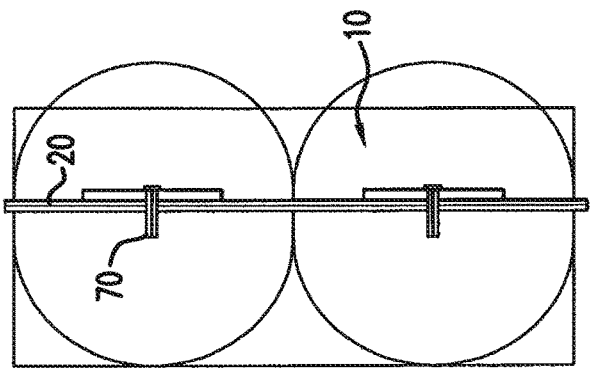
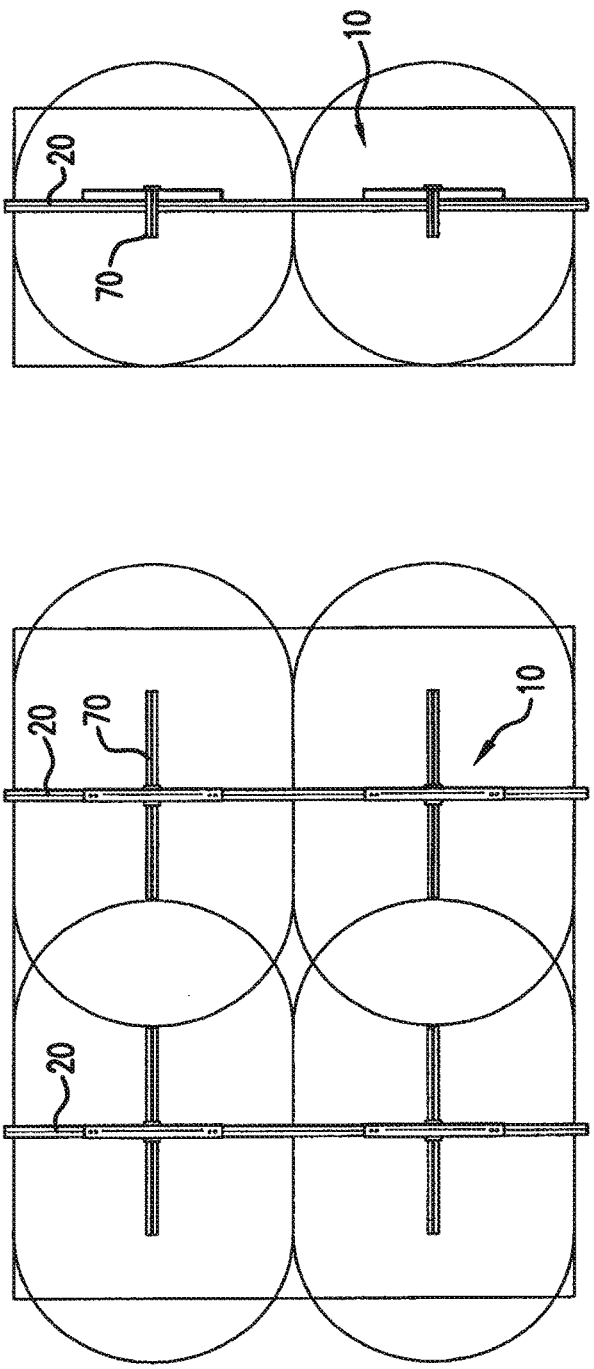

ULTRAVIOLET GERMICIDAL IRRADIATION SYSTEM

CROSS REFERENCE TO RELATED APPLICATIONS

This application is a continuation of U.S. application Ser. No. 13/742,035, filed Jan. 15, 2013; which is a continuation of U.S. application Ser. No. 13/229,293, filed Sep. 9, 2011, which is now U.S. Pat. No. 8,354,060, issued Jan. 15, 2013; which is a continuation of U.S. patent application Ser. No. 10/932,997, filed Sep. 2, 2004, which is now U.S. Pat. No. 8,038,949, issued Oct. 11, 2011 The disclosure of each of the above-referenced applications are hereby incorporated herein by reference in their entirety.

FIELD OF THE INVENTION

The present invention relates generally to an ultraviolet germicidal irradiation system for sterilization of microorganisms in various applications. More specifically, the present invention relates to an ultraviolet germicidal irradiation system for use in residential, commercial, and industrial heating, ventilation, and air-conditioning ("HVAC") applications.

BACKGROUND OF THE INVENTION

Contaminated air in buildings and homes is now an international issue. Certain airborne contaminants cause widespread discomfort and health problems, leading to absenteeism from school and work, as well as reduced productivity. Healthy and productive indoor environments would save billions of dollars in health care costs, lost work time, overall output and possible litigation.

Of the many contaminants found in indoor air, bioaerosols are regarded as the leading cause of allergies and other maladies referred to as SBS (Sick Building Syndrome) and BRI (Building-Related Illness). Bioaerosols are airborne products that include microorganisms, their fragments and spores, metabolic gases, and other toxins and waste products. Numerous studies have found high concentrations of these bioaerosols both in air handling equipment and the interiors they serve.

Airborne and surface microorganisms include pathogens, allergens, and toxins. Included in the category of pathogens are viruses, bacteria, and mold, which could cause measles, chicken pox, Legionnaires disease, aspergillosis, tuberculosis, and other infectious disease. Bacteria and mold are also classified as allergens because they can cause allergic rhinitis, asthma, humidifier fever and hypersensitivity pneumonitis. Toxins include mycotoxins and endotoxins, which can cause toxic and allergic reactions, irritations, and odors. Among allergens, mold and mold products are probably the most common worldwide.

Allergy tests universally bear out this phenomenon. In HVAC equipment, mold can proliferate year-round. With most individuals, prolonged exposure to mold and mold products initiates the release of histamines, causing inflammation of mucous membranes, which can be followed by congestion, breathing difficulties, asthma and other respiratory complications.

Conventional HVAC systems are an ideal source and conduit for the origin and/or spread of microorganisms. Their environments are especially conducive to amplifying molds and some bacteria. The fans of the HVAC system disseminate and/or recirculate system, space and occupant-generated microorganisms room to room and person to person. Conventional filtration assemblies of such HVAC systems are compromised because growth typically occurs downstream of filters, which allows microorganisms to seed in the ductwork and travel to and throughout the occupied space. Additionally, viruses and many bacteria are too small to be captured by a common air filter.

Traditional bioaerosol controls tend to be impractical, toxic, detrimental to equipment operation, and costly. Hence, the industry has turned to ultraviolet germicidal irradiation ("UVGI") for the sterilization of microorganisms. In HVAC systems, the application of UVGI in the air handling unit cooling coil and filter assemblies is effective in reducing the number of microorganisms. Additionally, the constant irradiation exposure has been found to be effective at controlling fungal growth.

Microbes are uniquely vulnerable to the effects of light at wavelengths at or near 2537 Angstroms, due to the resonance of this wavelength with molecular structures. A quantum of energy of ultraviolet light at these wavelengths possesses an amount of energy sufficient to break organic molecular bonds, which damages the cellular structure of the microorganisms.

The ultraviolet component of sunlight is the main reason microbes die in the outdoor air. The die off rate in the outdoors varies from one pathogen to another, but can be anywhere from a few seconds to a few minutes in order to kill 90 to 99% of viruses and contagious bacteria. Spores and some environmental bacteria tend to be resistant and can survive much longer exposures. UVGI systems use much more concentrated levels of ultraviolet energy than are found in sunlight.

The kill rate of pathogens and other microorganisms using UVGI depends on several factors, including UVGI intensity, the number of microorganisms present, and the amount of time the microorganisms are present in the UVGI zone, or dwell time. Generally, kill rate increases as the UVGI intensity is increased and/or the dwell time is increased.

SUMMARY

The invention described herein is a germicidal light grid system. In one example, the light grid system is positioned inside a plenum. The light grid system can be positioned adjacent to a cooling apparatus, such as, for example, an evaporative cooling coil. One can appreciate that such a light grid system is not limited for use inside a plenum, nor is it limited when used inside of a plenum to being positioned adjacent to cooling apparatuses. For instance, the light grid system can be used in plenums adjacent to air filtration banks, air intake vents, air mixing junctions, and/or plenum transition areas.

The light grid system of the present invention comprises at least one elongate member, at least one lamp assembly, and at least one germicidal light source. The at least one elongate member is mounted within a plenum in which a stream of air is entrained therein. In one aspect, the at least one elongate member can be connected to a portion of the plenum.

In one example of the light grid system, the at least one lamp assembly is mounted at a predetermined position on a portion of one of the elongate members. The predetermined position is operator selectable and can include any portion of the elongate length of the elongate member. Each lamp assembly comprises a housing defining at least one socket that extends at an acute angle relative to a transverse axis of the housing. The linear light source has a longitudinal axis and a distal end that is constructed and arranged to releasably mount within one socket of the housing. In use, each light source extends therein the stream of air such that the longitudinal axis of the light source is positioned at an acute light angle relative to the direction of flow of the stream of air.

BRIEF DESCRIPTION OF THE DRAWINGS

These and other features of the preferred embodiments of the present invention will become more apparent in the detailed description in which reference is made to the appended drawings wherein:

FIG. 1 is a top elevational view of one embodiment of the germicidal irradiation system of the present invention mounted therein a plenum.

FIG. 2 is a front elevational view of the germicidal irradiation system of FIG. 1.

FIG. 3 is a side elevational view of the germicidal irradiation system of FIG. 1.

FIG. 6 is a top elevational view of one embodiment of a lamp assembly of the germicidal irradiation system of the present invention spaced from a cross-sectional view of an exemplified elongate member, and showing a housing, at least one linear light source mounted therein sockets of the housing, the linear light source being angled at an acute angle α with respect to the transverse axis of the housing.

FIG. 7 is a front elevational view of the lamp assembly of FIG. 6 showing a ballast device disposed therein an internal cavity of the housing.

FIG. 8 is a side elevational view of the lamp assembly of FIG. 6, showing a flange member adapted to mount within a portion of an exemplified elongate member.

FIG. 9 is a top elevational view of an alternative embodiment of a lamp assembly of the germicidal irradiation system of the present invention spaced from a cross-sectional view of an exemplified elongate member, and showing a housing, at least one linear light source mounted therein sockets of the housing, the linear light source being angled at an acute angle α with respect to the transverse axis of the housing.

FIG. 10 is a front elevational view of the lamp assembly of FIG. 9 showing a ballast device disposed therein an internal cavity of the housing.

FIG. 11 is a side elevational view of the lamp assembly of FIG. 9, showing a flange member adapted to mount within a portion of an exemplified elongate member.

FIGS. 15-20 are top, front, and side elevational views of exemplary constructions of the germicidal irradiation system of the present invention showing the linear light source being positioned an the acute angle α with respect to the transverse axis of the housing and showing the lamp assembly being mounted to the elongate member such that the longitudinal axis of the light source extends therein the stream of air at an acute light angle relative to the direction of the flow of the stream of air entrained in the plenum. In one aspect, the longitudinal axis of the light source is positioned at an acute light angle θ relative to the common plane formed by a first elongate member and a second elongate member of a support assembly. In one aspect, the common plane formed by the first and second elongate members is substantially transverse to the direction of the flow of the stream of air.

DETAILED DESCRIPTION OF THE INVENTION

Figure 4:
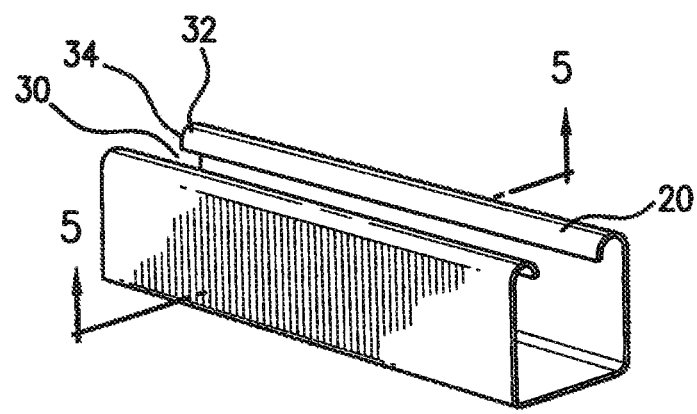
FIG. 4 is a perspective view of a portion of an exemplified elongate member of a support assembly of the present invention.

The present invention is more particularly described in the following exemplary embodiments that are intended as illustrative only since numerous modifications and variations therein will be apparent to those skilled in the art. As used herein, "a," "an," or "the" can mean one or more, depending upon the context in which it is used. The preferred embodiments are now described with reference to the figures, in which like reference characters indicate like parts throughout the several views.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

FIGS. 1-3 illustrate one embodiment of a modular germicidal light grid system 10. This embodiment of the light grid system is designed for use inside a plenum 2 in which a stream of air 4 is entrained and flows in a predetermined direction. The light grid system 10 can be positioned adjacent to a cooling apparatus 6, such as, for example, an evaporative cooling coil. One can appreciate that the light grid system 10 of the present invention is not limited for use inside a plenum, nor is it limited when used inside of a plenum to being positioned adjacent to cooling apparatuses. For instance, the light grid system 10 of the present invention can be used in plenums 2 adjacent to air filtration banks, air intake vents, air mixing junctions, and/or any plenum transition area.

In one aspect, the light grid system 10 comprises at least one elongate member 20, at least one lamp assembly 50, and at least one linear germicidal light source 70. The elongate member 20 is positioned within the plenum 2. Each lamp assembly 50 comprises a housing 52 having a transverse axis, as is shown in FIGS. 6-14. In one example of the light grid system 10, the transverse axis of the housing 52 is substantially perpendicular to a plane transverse to the direction of flow of the stream of air 4. However, the transverse axis of the housing 52 can be positioned in any desired relation to the direction of flow of the stream of air 4. The housing 52 defines at least one socket 54 that extends at an acute angle α relative to the transverse axis of the housing. A portion of the housing 52 of each lamp assembly is constructed and arranged to mount to a portion of the at least one elongate member 20 at a predetermined position that is operator selected. The predetermined position can, as one will appreciate, be any portion of the elongate length of the elongate member, as desired.

Each linear light source 70 has a longitudinal axis and a distal end 72 constructed and arranged to mount within one socket 54 of the housing. As one will appreciate, it is contemplated that the light source can be removeably replaced as maintenance requires. In one aspect, the at least one lamp assembly 50 is mounted to the at least one elongate light member 20 such that the longitudinal axis of the at least one light source 70 extends therein the stream of air and is positioned at an acute light angle relative to the direction of the flow of the stream of air 4.

In one aspect, the at least one elongate member forms 20 a part of a modular support assembly 22. In use, the modular support assembly 22 of the present invention provides for the economical and efficient construction of a support structure that can be dimensioned as desired to fit within the particular physical dimensions of the plenum 2. Prior germicidal light systems required a "custom fit" preparation of a support structure that increased the expense of the installed air treatment system and the lead time required for installation (for the actual physical construction of a "custom" structure).

In one example, the modular support assembly 22 of the present invention comprises at least one elongate first member 24 and at least one elongate second member 26 positioned substantially perpendicular to the elongate first member. One or more of the elongate first or second members 24, 26 can be connected to a portion of the plenum 2. In one aspect, the at least one elongate first member 24 and the at least one elongate second member 26 are positioned within a common plane. In one aspect, the housing 52 of the light assembly 50 can be mounted to the elongate member 24, 26 such that the transverse axis of the housing 52 is substantially perpendicular to the common plane of the elongate first and second members.

In one embodiment, the elongate second member 26 can be constructed from 1⅝" three walled strut type channel UL electrical raceway material. As one will appreciate, the elongate first member 24 can also be constructed from the same material. Using conventional raceways that can be mounted to each other with conventional fasteners and/or mounts allows for expedient construction of the support assembly. As one will appreciate, these are merely representative examples of construction materials and methodologies. For example, the elongate first and second members 24, 26 can be connected in any of a number of ways, such as, for example, with conventional fasteners.

In one aspect, the at least one linear germicidal light source 70 extends such that the longitudinal axis of the light source is positioned at an acute light angle θ, relative to the common plane formed by the first and second elongate members 24, 26. In one aspect, the common plane formed by the first and second elongate members 24, 26 is substantially transverse to the direction of flow of the stream of air 4. The linear light sources 70 can be, for example, 22" double arc length 4-pin germicidal lamps, such as the TUV PL-L 55W/HF made by Philips™. However, as one skilled in the art will appreciate, any elongate ultraviolet germicidal lamp can be used.

In one example of the system, the preferred acute light angle θ is about 10° to less than about 90°. More preferably, the acute light angle θ is between about 20° to about 80°. Even more preferred, the acute light angle θ is between about 30° to about 70°. Still more preferred, the acute light angle θ is about 30°, or alternatively, about 45°.

In one example, at least one elongate first member 24 is spaced at predetermined distance from the cooling apparatus 6. In another aspect, at least one elongate second member 26 can be positioned at the same predetermined distance from the cooling apparatus 6, or, alternatively, can be at a different predetermined distance. In one example of the light grid system, the predetermined distance is preferably between about 3" and about 24". More preferably, the predetermined distance is between about 5" and about 20". Still more preferred, the predetermined distance is about 18". Alternatively, the predetermined distance is about 12". In still another alternative aspect, the predetermined distance is about 6".

As is depicted in FIG. 1, in one example of the light grid system 10 each socket 54 of the housing 52 has a longitudinal axis that is oriented rearwardly away from the cooling apparatus 6. In yet another example, each socket 54 of the housing 52 has a longitudinal axis that is oriented forwardly toward the cooling apparatus 6. In still another example, the light grid system 10 has at least one socket 54 oriented rearwardly away from the cooling apparatus 6 and at least one socket 54 oriented forwardly toward the cooling apparatus 6.

As shown in FIGS. 10-13, in one embodiment, the light grid system 10 of the present invention further comprises a power supply 80 and at least one ballast device 82 electrically coupled to the power supply and the at least one socket 54 of the housing. In one aspect, the housing of each light assembly can define an internal cavity 56 that is sized and shaped for the at least one ballast device 82 to be disposed therein. In another example, the ballast device 82 is located at a remote location spaced from the housing. The ballast device 82 can be electrically coupled to the power supply 80 conventionally, for example, by using conventional 3 or 6 stranded electrical wires.

One example of the ballast device 82 is a solid-state, non-potable, high frequency ballast operating at about either 120 or 277 volts AC and at about 50 to 60 Hz. For exemplary lamp assemblies 50 with two germicidal light sources, a single uniform ballast allows for subsequent simplicity for inventory and change requirements by the end user. In one aspect of the ballast device 82, the ballast device is self-regulating with direct current output. In one aspect, the ballast device 82 for the exemplary two light source lamp assembly 50 can deliver up to about 110 watts to each lamp or about 220 watts total. In one aspect, the ballast device 82 for an exemplary one light source lamp assembly 50 can deliver up to about 140 watts to the lamp.

In practice, the housing that contains the ballast device 82 can be pre-wired for connection to the remote power supply 80. In this example, the ballast device 82 can include a wiring assembly 84 that extends from the internal cavity 56 of the housing through a port 58 defined in the housing 52. In this example, the support assembly 22 and the at least one lamp assembly 50 mounted thereto, can be constructed completely by the installer. Then, after the construction is complete, an electrician can electrically connect the wiring assembly 84 extending from the mounted lamp assemblies 50 to the power supply by coupling the wiring assembly 84 to the electrical wire 81 that extends to the power supply 80.

Figure 14:
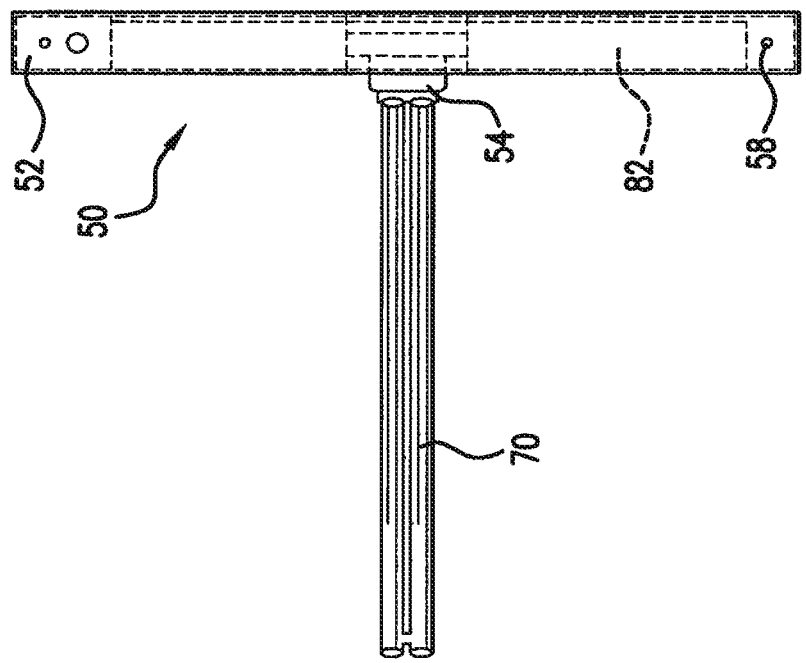
FIG. 14 is a front elevational view of the lamp assembly of FIG. 12 showing a ballast device disposed therein an internal cavity of the housing.
Figure 13:
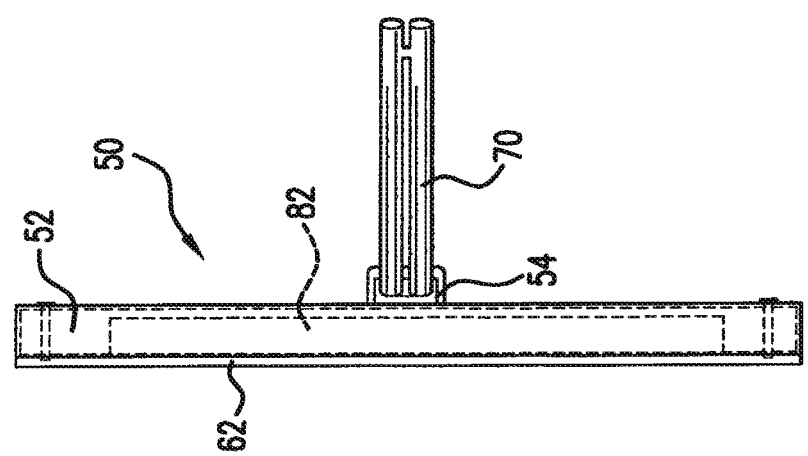
FIG. 13 is a side elevational view of the lamp assembly of FIG. 12, showing a flange member adapted to mount within a portion of an exemplified elongate member.
Figure 18:
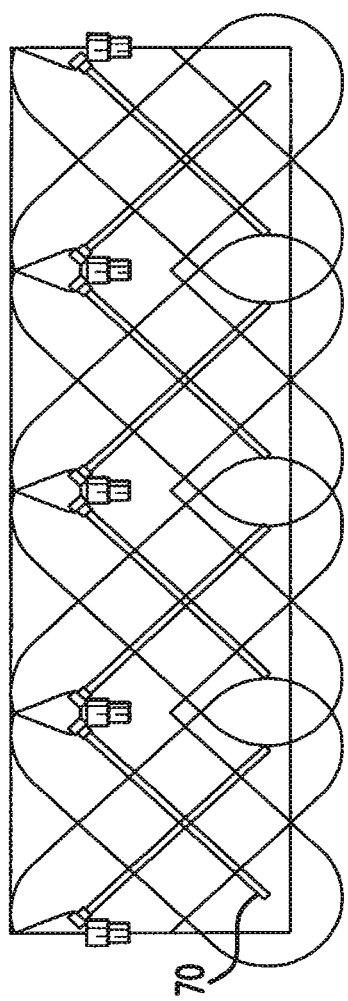
Figure 20:
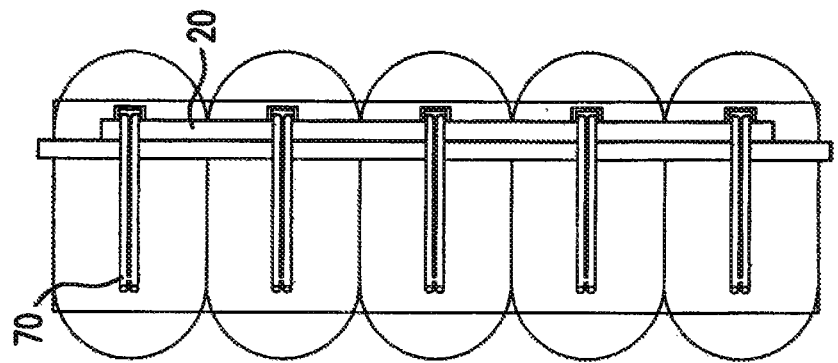
Figure 19:
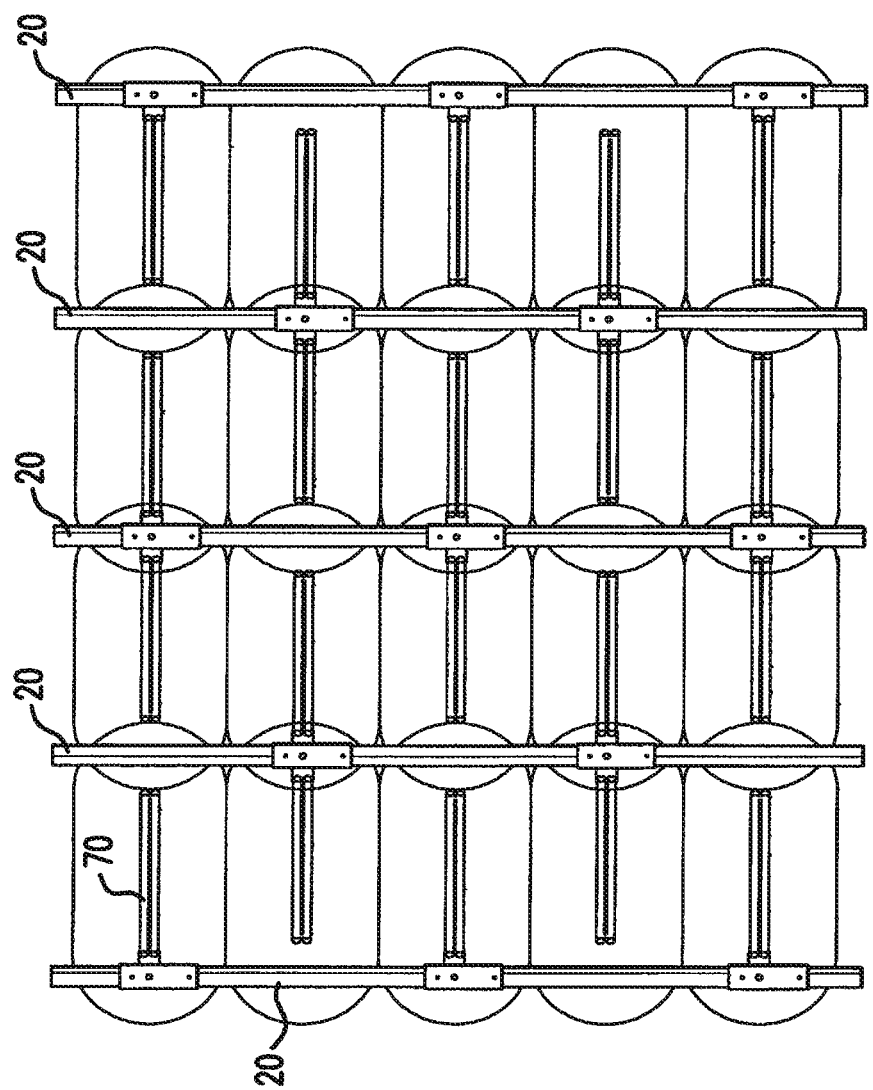

FIGS. 6, 9 and 14 show an example of the lamp assembly in which the lamp assembly 70 is releasably mounted to the elongate member, for example, a second elongate member 26, of the support assembly. As one will appreciate, having the lamp assembly 70 releasably attached to the elongate member 20 provides for convenient installation and disassembly. However, it will be appreciated that any number of attachment techniques including providing permanent attachments are contemplated.

Figure 5:
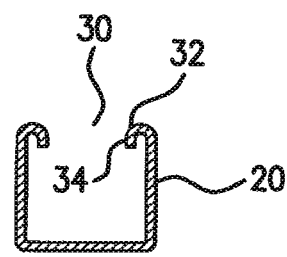
FIG. 5 is a cross-sectional view of the elongate member of FIG. 4 taken across section 5-5.
Figure 12:
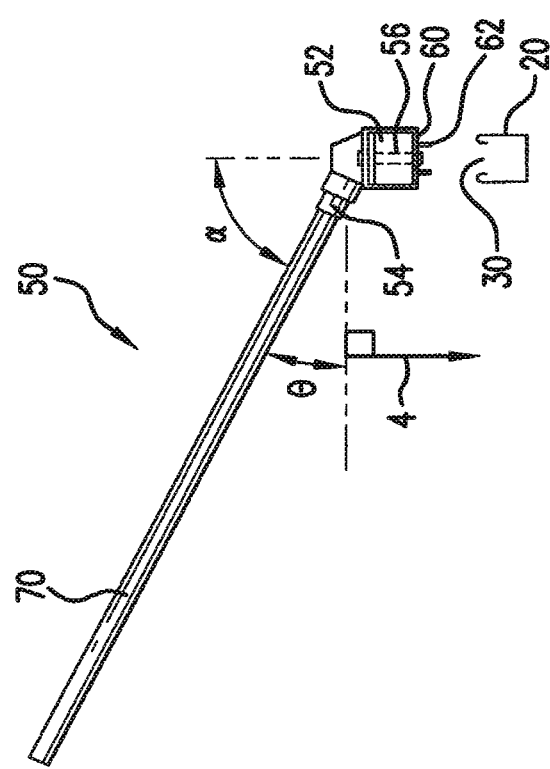
FIG. 12 is a top elevational view of an alternative embodiment of a lamp assembly of the germicidal irradiation system of the present invention spaced from a cross-sectional view of an exemplified elongate member, and showing a housing, a linear light source mounted therein a socket of the housing, the linear light source being angled at an acute angle α with respect to the transverse axis of the housing.

FIGS. 4 and 5 illustrate an example of the support assembly 22 in which the elongate second member 26 and/or the elongate first member 24 defines a trough 30. Further, a portion of the housing 52 is sized and shaped for disposition within a portion of the trough 30 of the elongate member 20. In one example, the elongate second member 26 can have a substantially U-shape in cross-section. As one skilled in the art will note, the elongate member 20 can have any number of varied cross-sectional shapes, including, for example, a V-shape, a C-shape, and the like. In one aspect, a portion of the housing 52 is adapted for a friction fit within the portion of the trough 30 of the elongate member 20.

Figure 23:
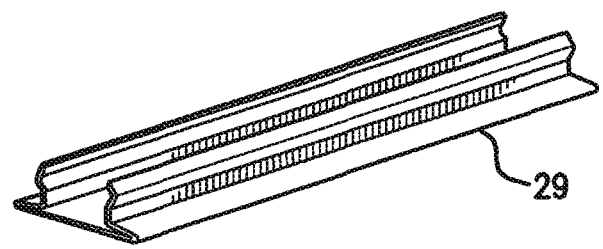
FIG. 23 is a perspective view of a flange member of a housing of the light assembly of the present invention.

In this embodiment, the trough 30 acts as a conduit that is adapted for disposition of wiring that couples the power supply 80 to the ballast device 82 and subsequently to the at least one socket 54 of the housing. Additionally, as exemplified in FIG. 23, a closure strip 29 can be provided to seal the open portion of the trough 30 after wiring of the light grid system 10 is complete to seal the inside of the trough from the ambient environment. Thus, the formed conduit acts as an electrical raceway that enables the system assembler to conceal any necessary electrical wires.

FIGS. 4 and 5 also show an example wherein the elongate second member 26 defines a trough 30 that has a pair of opposing, longitudinally extending, edges 32 that bend inwardly to form a pair of opposing male protrusions 34. A portion of the housing 52 is sized and shaped for disposition within a portion of the trough 30. In one aspect, the portion of the housing 52 defines an elongate flange member 60 having a pair of longitudinally extending, opposing male protrusions 62. The opposing male protrusions 62 of the flange member 60 are sized and shaped for overlying registration within the portion of the trough 30 of the elongate second member 26. As one will appreciate, the pair of opposing male protrusions 62 of the flange member 60 can be adapted for a friction fit with the portion of the trough 30.

In one aspect, and as exemplified in the figures, the housing 52 is positioned on an elongate second member 26 using a snap-fit connection. This configuration allows the independent installation of the support assembly and lamp assembly to be constructed by non-electrically qualified personnel such as mechanical contractors. Once the support assembly 22 is constructed and the lamp assemblies 50 are mounted thereon, a second independent installation of the electrical components can be completed by qualified electrical contractors. Additionally, the snap in feature used in this example allows the electrical contractor to wire the lamp assembly without dismantling the housing 52. It also enables the end user to quickly remove and replace the lamp assembly.

Figure 21:
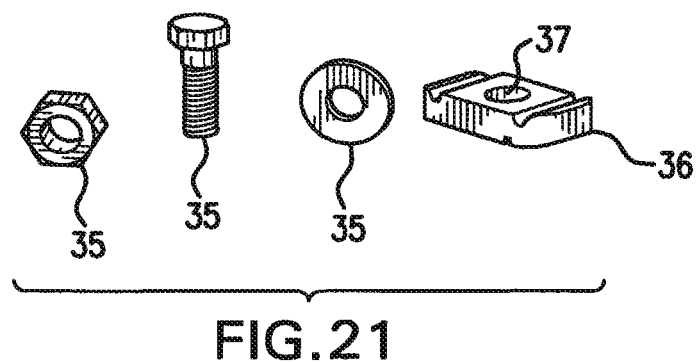
FIG. 21 are perspective views of an exemplary fastener and planar member for connecting the housing of the light assembly to an elongate member.

Another example of the light grid system 10 is shown in FIGS. 4, 5 and 21. Here, the pair of opposing male protrusions 34 of the trough 30 are spaced apart a predetermined distance. This predetermined distance, for example, preferably can be between about ½" and 2". More preferably, the predetermined distance is about ⅞". In this example, the second elongate member 26 further comprises a fastener 35 coupled to the housing 52 of the light assembly and a planar member 36 that defines a bore 37. The planar member 36 in this example has a dimension greater than the predetermined distance and is sized and shaped for positioning within a portion of the trough 30. In this example, the fastener 35 and the bore 37 are complementarily sized and shaped so that, in use, the fastener engages the bore of the planar member to force a portion of the planar member into contact with a portion of the pair of opposing male protrusions 34. This acts to secure the housing 52 of the light assembly 50 in the predetermined position on the elongate member.

Figure 22:
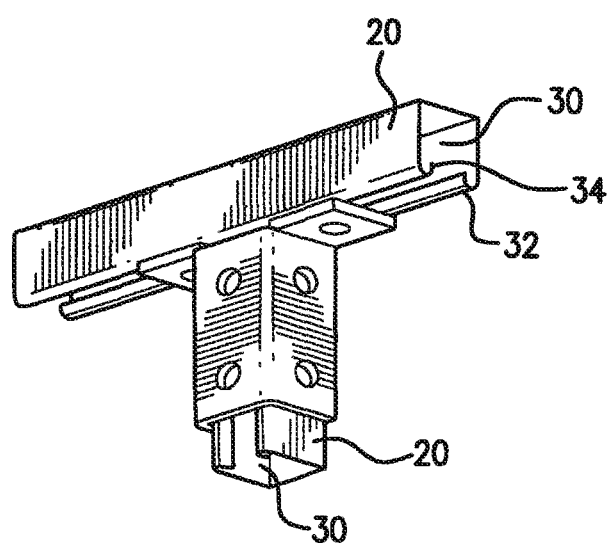
FIG. 22 is a perspective view of one embodiment of a mount for connecting a first elongate member of the support assembly to a portion of a second elongate member of the support assembly.

FIG. 22 illustrates one embodiment of a light grid system 10 in which the elongate second member 26 is slidably mounted to the elongate first member 24. This allows for rapid adjustment of the elongate second member with respect to the elongate first member should it be needed. It is contemplated that the second elongate member can be releasably fixed to the first elongate member when the respective elongate members are at their desired positions.

Figure 24:
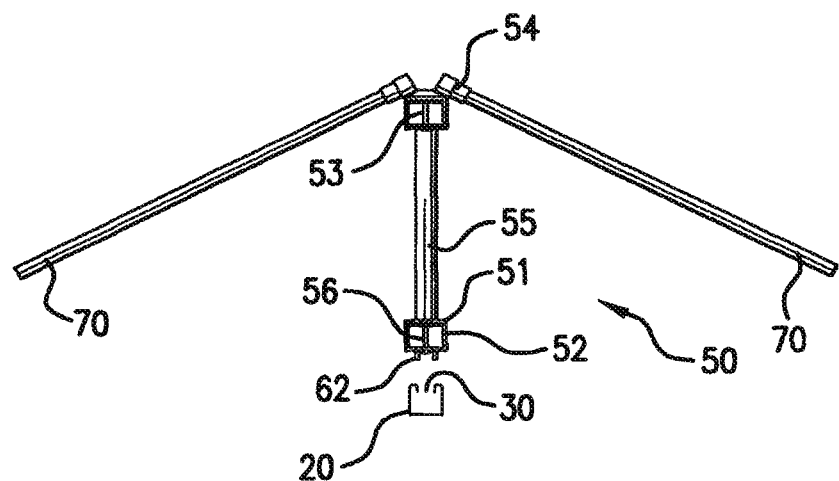
FIG. 24 is a top elevational view of an alternative embodiment of a lamp assembly of the germicidal irradiation system of the present invention spaced from a cross-sectional view of an exemplified elongate member, and showing a first body, a second body, and an elongate conduit extending therebetween, and showing a linear light source mounted therein a socket of the second body of the housing, the linear light source being angled at an acute angle α with respect to the transverse axis of the housing.
Figure 25:
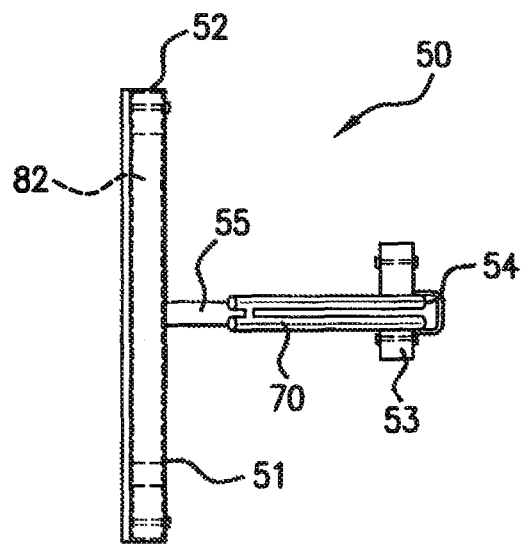
FIG. 25 is a side elevational view of the lamp assembly of FIG. 24, showing a flange member adapted to mount within a portion of an exemplified elongate member.

In an alternative embodiment of the lamp assembly 50, as shown in FIGS. 24 and 25, the housing 52 of the lamp assembly comprises a first body member 51, an opposed second body member 53, and an extension conduit 55 connected to and extending there between the first and second body members. In one aspect of this embodiment, the extension conduit extends substantially coaxial to the transverse axis of the housing. The at least one socket 54 is defined on the second body member 53. A portion of the first body member 51 of the housing 52 is constructed and arranged to mount to the portion of the elongate member as described above. In a further aspect, the first body defines the mutual cavity 56 sized and sloped for the at least one ballast device 82 to be disposed therein.

As noted above, the light grid system 10 of the present invention is constructed to be positioned inside of a plenum 2 in which a stream of air 4 is entrained. The stream of air has a direction of flow, in which contaminants and pathogens may exist. Positioning the light sources 70 at an acute light angle, θ, relative to the common plane formed by the two elongate members, wherein the plane is perpendicular to direction of flow, increases the distance the contaminants and or pathogens must travel inside of the UVGI zone. Thus, the microbial dwell time inside the UVGI zone is increased, providing for a higher kill rate of pathogens or contaminants as compared to a system in which θ is 0° or 90°.

In another aspect, the angle at which the lamps are positioned is determined by the acute angle α, at which the socket extends relative to the transverse axis of the housing. In one preferred example of the light grid system, the acute angle α, is about 10° to less than about 90°. More preferably, acute angle α is between about 20° to about 80°. Even more preferred, acute angle α is between about 30° to about 70°. Still more preferably, acute angle α is about 45°, or alternatively, is about 60°.

Also disclosed is a performance standard for the measuring UVGI in a germicidal light grid system. These UVGI factors are calculated using the Inverse Square Law, which can be written $$I = \frac{S}{4\pi r^2},$$

wherein I is the intensity of the influence, S is the source strength and r is the distance from the source. For convenience, four levels of performance capability are disclosed. They are as follows:

Level 1: Minimum UVGI factor of 9.
Level 2: Minimum UVGI factor of 16.
Level 3: Minimum UVGI factor of 36.
Level 4: Minimum UVGI factor of 144.

The primary function of a system at Level 1 is the surface disinfection of stationary devices. The secondary function of Level 1 is for the deactivation of microbial agents in dynamic motion within a moving airstream. For the purpose of ease of discussion, in this and all of the following discussions regarding performance capabilities, we assume that there are two germicidal light sources 70 per lamp assembly 50 and that the light sources used are the aforementioned Philips™ germicidal lamps. As such, in one example, the spacing of the germicidal light sources 70 along the elongate second member 26 is about 48" in order to maintain a UVGI factor of 9. Exemplary spacing between germicidal light sources 70 on separate elongate second members 26 is about 24" in order to maintain a UVGI factor of 9.

The primary function of Level 2 capability is for the deactivation of microbial agents in dynamic motion within a moving airstream. The secondary function of Level 2 is for the disinfection of stationary sources, typically air-handling system components. In one example, vertical spacing of the germicidal light sources along the elongate second member is about 36" in order to maintain a UVGI factor of 16. Exemplary spacing between germicidal light sources on separate elongate second members is about 18" in order to maintain a UVGI factor of 16.

The primary function of Level 3 capability is for the deactivation of microbial and pathogenic agents in dynamic motion within a moving airstream. The secondary function of Level 3 is for surface disinfection of stationary devices, typically mission critical process filtration air-handling system components. For example, vertical spacing of the germicidal light sources along the elongate second member is about 24" in order to maintain a UVGI factor of 36. Exemplary spacing between germicidal light sources on separate elongate second members is about 12" in order to maintain a UVGI factor of 36.

The primary function of Level 4 capability is for the deactivation of microbial and pathogenic agents in dynamic motion within an airstream. The secondary function of Level 4 is for surface disinfection of stationary devices, typically mission critical process filtration air-handling system components. In one example, vertical spacing of the germicidal light sources along the elongate second member is about 12" in order to maintain a UVGI factor of 144. Here, the germicidal lamps on separate elongate second members are crossed, with an example being between them of about 6" in order to maintain a UVGI factor of 144.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A modular germicidal light grid system for use inside a plenum downstream of a cooling apparatus, the system comprising:
   a support assembly comprising:
   at least one elongate first member; and
   at least one elongate second member mounted and positioned substantially perpendicular to the at least one elongate first member; and
   at least one lamp assembly, each lamp assembly constructed and arranged to mount to at least a portion of the at least one elongate second member of the support assembly, each lamp assembly comprising a linear germicidal light source having a longitudinal axis,
   wherein the at least one elongate first member and the at least one elongate second member are positioned within a common plane, and wherein the linear germicidal light source of each lamp assembly extends such that the longitudinal axis of the linear germicidal light source is positioned at an acute light angle relative to the common plane.

2. The modular germicidal light grid system of claim 1, wherein each lamp assembly further comprises a housing defining at feast one socket for operative, mounting of the linear germicidal light source.

3. The modular germicidal light grid system of claim 2, wherein each light source has a distal end constructed and arranged to mount within one socket of the housing.

4. The modular germicidal light grid system of claim 2, wherein the housing of each lamp assembly has a transverse axis, and wherein the transverse axis of the housing is substantially perpendicular to the common plane.

5. The modular germicidal light grid system of claim 4, wherein each socket of the housing extends at an acute angle relative to the transverse axis of the housing.

6. The modular germicidal light grid system of claim 4, wherein the housing of the at least one lamp assembly comprises a first body member, an opposed second body member, and an extension conduit connected to and extending between the first and second body members, wherein the extension conduit extends substantially coaxial to the transverse axis of the housing, wherein the at least one socket is defined on the second body member, and wherein a portion of the first body member of the housing is constructed and arranged to mount to the portion of the at least one elongate second member.

7. The modular germicidal light grid system of claim 2, further comprising a power supply and at least one ballast device electrically coupled to the power supply and the linear germicidal light source.

8. The modular germicidal light grid system of claim 7, wherein the housing defines an internal cavity, and wherein the at least one ballast device is disposed therein the internal cavity.

9. The modular germicidal light grid system of claim 2, further comprising a power supply and at least one ballast device electrically coupled to the power supply and the at least one socket of the housing.

10. The modular germicidal light grid system of claim 9, wherein the housing defines an internal cavity, and wherein the at least one ballast device is disposed therein the internal cavity.

11. The modular germicidal light grid system of claim 2, wherein the at least one elongate second member defines to trough, and wherein a portion of the housing is sized and shaped for disposition within a portion of the trough of the at least one elongate second member.

12. The modular germicidal light grid system of claim 1, wherein the at least one lamp assembly is releasably mounted to the at least one elongate second member of the support assembly.

13. The modular germicidal light grid system of claim 1, wherein at least one of the respective at least one elongate first and second members is connected to a portion of the plenum.

14. The modular germicidal light grid system of claim 13, wherein at least one of the at least one elongate first member is connected to an interior surface of the plenum.

15. The modular germicidal light grid system of claim 13, wherein the at least one elongate second member is slidably mounted to the at least one elongate first member.

16. The modular germicidal light grid system of claim 1, wherein the acute light angle is between about 10° to less than about 90°.

17. The modular germicidal light grid system of claim 1, wherein the acute light angle is between about 20° to about 80°.

18. The modular germicidal light grid system of claim 1, wherein the acute light angle is between about 30° to about 70°.

19. The modular germicidal light grid system of claim 1, wherein the acute light angle is about 60°.

20. The modular germicidal light grid system of claim 1, wherein the acute light angle is about 45°.

* * * * *